US00PP22671P2

(12) United States Plant Patent
Korlipara

(10) Patent No.: US PP22,671 P2
(45) Date of Patent: Apr. 17, 2012

(54) ***COREOPSIS* PLANT NAMED 'SHOW STOPPER'**

(50) Latin Name: ***Coreopsis* spp.**
Varietal Denomination: Show Stopper

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/931,224

(22) Filed: Jan. 26, 2011

(51) Int. Cl.
*A01H 5/00* (2006.01)

(52) U.S. Cl. ..... Plt./417

(58) Field of Classification Search ..... Plt./417
See application file for complete search history.

*Primary Examiner* — Annette Para

(74) *Attorney, Agent, or Firm* — Klarquist Sparkman, LLP

(57) ABSTRACT

A new and distinct *Coreopsis* plant named 'Show Stopper' characterized by prolific bloom of red purple daisy-type inflorescences, each about 5 cm wide, with excellent perennial survival, and a large mounding plant.

1 Drawing Sheet

Botanical denomination: *Coreopsis* spp.

Variety designation: 'Show Stopper'.

Parentage: *Coreopsis verticillata*×*Coreopsis* 'Limerock Ruby'.

Cross reference to: *Coreopsis* 'Center Stage' (U.S. Plant patent application Ser. No. 12/931,225).

BACKGROUND OF THE INVENTION

The present invention relates to a new and distinct hybrid of *Coreopsis* and given the cultivar name 'Show Stopper'. *Coreopsis* is in the family Asteraceae. This new cultivar originated from a controlled cross of *Coreopsis verticillata*, an unpatented plant, as the seed parent and *Coreopsis* 'Limerock Ruby', U.S. Plant Pat. No. 15,455, as the pollen parent.

Compared to the seed parent, *Coreopsis verticillata*, the new hybrid has rose magenta inflorescences rather than yellow. Compared to the pollen parent, *Coreopsis* 'Limerock Ruby', U.S. Plant Pat. No. 15,455, the new cultivar is larger in size and is Zone 6 hardy rather than Zone 9 hardy.

Compared to its sibling, *Coreopsis* 'Center Stage', the new cultivar has rose magenta inflorescences rather than dark red.

Compared to *Coreopsis* 'Heaven's Gate', U.S. Plant Pat. No. 16,016, the new cultivar has deeper pink inflorescences.

SUMMARY OF THE INVENTION

The following traits have been repeatedly observed and are determined to be the unique characteristics of the new variety. These characteristics in combination distinguish *Coreopsis* 'Show Stopper' as a new and distinct cultivar:

1. prolific bloom and rebloom of rose magenta daisy-type inflorescences,
2. inflorescences about 5 cm in diameter,
3. excellent perennial survival (hardy to USDA Zone 6),
4. and a large mounding habit.

This new cultivar has been reproduced only by asexual propagation (cuttings and tissue culture). Each of the progeny exhibits identical characteristics to the original plant. Asexual propagation by cuttings and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE PHOTOGRAPH

The photograph shows a one-year-old *Coreopsis* 'Show Stopper' growing in the ground in the trial field in August in Canby, Oreg.

DETAILED PLANT DESCRIPTION

The following is a detailed description of the new *Coreopsis* cultivar based on observations of a one-year-old specimen growing in the ground in full sun under typical outdoor conditions in the trial fields in August in Canby, Oreg.. Canby is Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart, $4^{th}$ edition.

Plant:

*Type*.—Herbaceous perennial.
*Hardiness*.—USDA Zones 6 to 9.
*Size*.—45 cm wide and 35 cm tall to top of inflorescences (will grow bigger in future years).
*Form*.—Loose mound.
*Vigor*.—Excellent.
*Roots*.—Fibrous, Grey Brown 199D, stems root easily from stem cuttings.

Stem:

*Type*.—Ascending.
*Size*.—35 cm tall and 4 mm wide.
*Branching*.—About 5 branches from the base, each stem branching further.
*Internode length*.—2.5 cm to 5.5 cm.
*Surface*.—Glabrous.
*Color*.—Yellow Green 137A.

Leaf:

*Type*.—Simple.

*Shape*.—Linear to oblanceolate with linear to oblanceolate lobes.

*Size*.—Leaves grow from 40 mm to 50 mm long and 1.5 mm to 4 mm wide, if lobed the leaf spread grows to 56 mm.

*Lobing on all but basal leaves*.—0 to 2 lobes, linear, each lobe 7 mm to 38 mm long and 1 mm to 2.5 mm wide.

*Arrangement*.—Opposite.

*Margins*.—Entire.

*Apex*.—Acute.

*Surface texture*.—Glabrous on both sides.

*Venation*.—Pinnate.

*Color*.—Yellow Green 147A on top side, Yellow Green 147B on bottom side.

Inflorescence:

*Type*.—Composite on terminal stalked heads.

*Peduncle*.—4.5 cm to 8.5 cm tall, 1 mm wide, glabrous, Yellow Green 137A.

*Size*.—Grows to 56 mm wide and 8 mm deep.

*Form*.—Ray florets held horizontally, mature disc is conic.

*Immature inflorescence*.—Ovoid, 7 mm wide and 7 mm deep, with inner phyllaries holding the florets, glabrous, bottom half Green 137A, top half Greyed Orange 165A and 166A.

*Ray florets*.—Without pistil or stamen, 8 in number, sometimes overlapping, grows to 28 mm long and 9 mm wide, obovate, entire, with the tip three lobed, the terminal lobe the longest, acute, glabrous on both sides; color topside closest to Red Purple 71A, darker and richer when first open and lightening to Purple 78A with maturity; bottom side closest to Violet 84A.

*Disc*.—Slightly convex becoming conic, becoming 5 mm long and 8 mm wide with maturity, background color is Greyed Orange 172A, with prominent stigmas, Orange 24A.

*Disc florets*.—About 90 in number, each 8 mm long and 1.5 mm wide; corolla 5.5 mm long and 1 mm wide, tubular, 4-lobed, glabrous, Yellow Orange 15C to 15D on the tube and backs of lobes, inside reflexed lobes Greyed Orange 172A; pistil 8 mm long, ovary 1.5 mm long, Green Yellow 1D, style 5 mm long, Yellow Orange 15A, with an extruding, 2-branched stigma, Orange 24A; stamen 4 in number, 3 mm long, anthers 2 mm long and Black 202A, filaments 1 mm long, Yellow Orange 15D, pollen Yellow 12A.

*Phyllaries*.—In 2 leafy campanulate series, area 15 mm wide and 6 mm deep; inner series 8 overlapping lobes, ovate, reflexed, margin entire, tips acute, glabrous on both sides, grow to 8 mm long and 3 mm wide, Yellow Green 147A on bottom half and Yellow Green 153C on top half; outer series smaller, 8 lobes, lanceolate, margins entire, tips acuminate, 3 mm long and 1.5 mm wide, glabrous on both sides, Yellow Green 147A.

*Bloom period*.—July through September in Canby, Oreg.

*Fragrance*.—None.

*Lastingness*.—Each inflorescence lasts about two weeks in Canby, Oreg.

Seeds: None.

*Fertility*.—Sterile.

Disease and pests: *Coreopsis* are susceptible to mildew and fungal spots. No resistances are known for this variety.

I claim:

1. A new and distinct *Coreopsis* plant as herein illustrated and described.

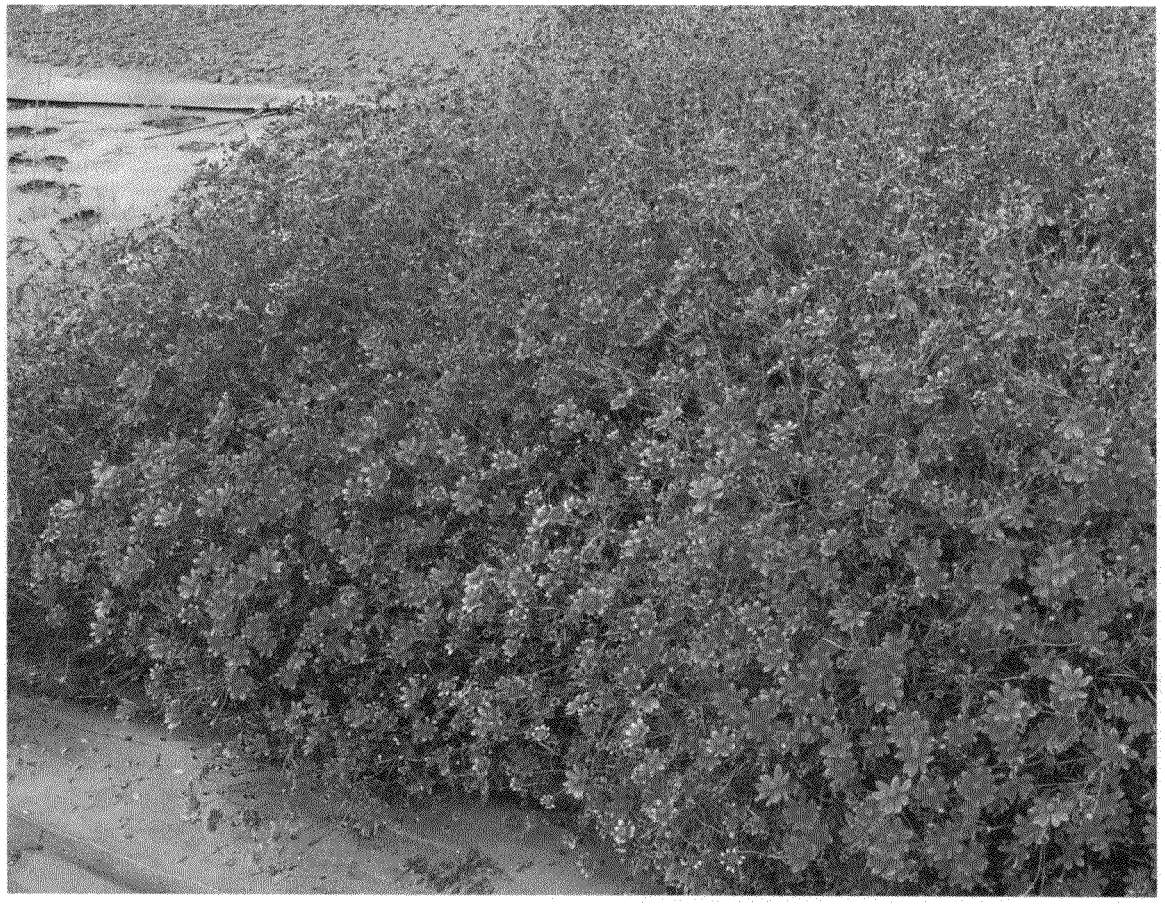

* * * * *